US012766294B2

(12) United States Patent
A. et al.

(10) Patent No.: US 12,766,294 B2
(45) Date of Patent: Oct. 20, 2026

(54) CATHETER SYSTEM HAVING A NEEDLE RETRACTION MECHANISM

(71) Applicant: Becton, Dickinson and Company, Franklin Lakes, NJ (US)

(72) Inventors: Edwin Jeyaseelan A., Tamil Nadu (IN); Balaji Kannan, Bangalore (IN)

(73) Assignee: Becton, Dickinson and Company, Franklin Lakes, NJ (US)

( * ) Notice: Subject to any disclaimer, the term of this patent is extended or adjusted under 35 U.S.C. 154(b) by 957 days.

(21) Appl. No.: 18/072,216

(22) Filed: Nov. 30, 2022

(65) Prior Publication Data

US 2024/0173522 A1 May 30, 2024

(51) Int. Cl.
*A61M 25/00* (2006.01)
*A61M 25/06* (2006.01)

(52) U.S. Cl.
CPC .... *A61M 25/0631* (2013.01); *A61M 25/0097* (2013.01); *A61M 25/0606* (2013.01)

(58) Field of Classification Search
CPC .. A61M 25/0631; A61M 25/06; A61M 25/01; A61M 25/0618; A61M 25/00; A61M 25/0693; A61M 25/0097; A61M 25/0606; A61M 39/10; A61M 25/0637
See application file for complete search history.

(56) References Cited

U.S. PATENT DOCUMENTS 4,863,435 A 9/1989 Sturman
4,921,490 A * 5/1990 Spier .................. A61M 5/3243 604/263
5,059,180 A 10/1991 McLees
5,092,851 A 3/1992 Ragner
5,292,314 A 3/1994 D'Alessio et al.
(Continued)

FOREIGN PATENT DOCUMENTS

WO 9924092 A1 5/1999
WO 02066093 A2 8/2002
WO 2006070358 A2 7/2006

OTHER PUBLICATIONS

Becton Dickinson and Company. (n.d.). BD InsyteTM AutoguardTM shielded IV catheter. BD. https://www.bd.com/en-ca/offerings/capabilities/infusion-therapy/iv-catheters/bd-insyte-autoguard-shielded-iv-catheter.

*Primary Examiner* — Chelsea E Stinson
*Assistant Examiner* — Hamza A Darb
(74) *Attorney, Agent, or Firm* — Kirton McConkie; Whitney Blair; Kevin Stinger

(57) ABSTRACT

A catheter system may include a catheter assembly, which may include a catheter adapter and a catheter. The catheter system may include a needle assembly, which may include a barrel, an introducer needle, a needle hub affixed to the introducer needle, and a spring disposed around the needle hub. The needle assembly may include a push button for selective engagement with the needle hub, and a distally-extending arm contacting the barrel. The needle hub may include a distally-extending arm forming a push button within a side hole of the barrel. The needle assembly may include a telescopic barrel, which may include an inner sleeve having a distally-extending arm forming a push button within a side hole of a main barrel. The needle assembly may include a lever arm coupled to the barrel. In response to depression of the lever arm, the lever arm may release a flexible extension of the needle hub.

11 Claims, 18 Drawing Sheets

(56) References Cited

U.S. PATENT DOCUMENTS

| | | | | |
|---|---|---|---|---|
| 5,501,675 | A | 3/1996 | Erskine | |
| 6,217,559 | B1 | 4/2001 | Foster | |
| 7,118,552 | B2 | 10/2006 | Shaw et al. | |
| 2011/0306933 | A1* | 12/2011 | Djordjevic ........ | A61M 25/0631 604/164.08 |
| 2012/0016307 | A1* | 1/2012 | Burkholz ......... | A61B 5/150916 604/168.01 |
| 2013/0310750 | A1* | 11/2013 | Hopman ............ | A61B 17/3496 604/159 |
| 2020/0001050 | A1 | 1/2020 | Garrison et al. | |

* cited by examiner

CATHETER SYSTEM HAVING A NEEDLE RETRACTION MECHANISM

BACKGROUND

A common type of catheter assembly includes a peripheral intravenous catheter ("PIVC") that is over-the-needle. As its name implies, the PIVC that is over-the-needle may be mounted over an introducer needle having a sharp distal tip. The catheter assembly may include a catheter adapter, the PIVC extending distally from the catheter adapter, and the introducer needle extending through the PIVC. The PIVC and the introducer needle may be assembled such that the distal tip of the introducer needle extends beyond the distal tip of the PIVC with the bevel of the needle facing up away from skin of the patient immediately prior to insertion into the skin. The PIVC and the introducer needle are generally inserted at a shallow angle through the skin into vasculature of the patient.

In order to verify proper placement of the introducer needle and/or the PIVC in the blood vessel, a clinician may confirm that there is flashback of blood in a flashback chamber of the catheter assembly or in a space between the introducer needle and the PIVC. Once placement of the introducer needle has been confirmed, the clinician may remove the introducer needle, leaving the PIVC in place for future blood withdrawal or fluid infusion.

In some instances, the catheter assembly, such as, for example, the BD INSYTE™ AUTOGUARD™ Shielded IV Catheter, available from Becton Dickinson and Company of Franklin Lakes, New Jersey, may include a push button configured to retract the introducer needle after the PIVC is in place within the vein. A common problem with this type of retraction mechanism is blood splatter due to rapid and/or non-linear retraction of the introducer needle after depression of the push button. The blood splatter may contribute to increased occurrences of blood-borne virus exposures. Silicon gel is often used as a damper to delay a release time of a spring configured to retract the introducer needle, which may reduce the blood splatter. The silicon gel, however, may be messy and/or difficult to apply.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to vascular access. More particularly, the present disclosure relates to a catheter system that includes a needle retraction mechanism, as well as related devices and methods. In some embodiments, the needle retraction mechanism may be configured to reduce blood splatter and thereby reduce a risk of exposure to blood-borne viruses. A first set of embodiments is now described. In some embodiments, a catheter system may include a catheter assembly, which may include a catheter adapter. In some embodiments, the catheter adapter may include a distal end, a proximal end, and a catheter adapter lumen extending through the distal end of the catheter adapter and the proximal end of the catheter adapter. In some embodiments, the catheter system may include a catheter extending from the distal end of the catheter adapter.

In some embodiments, the catheter system may include a needle assembly, which may include a barrel. In some embodiments, the barrel may include a proximal end and a distal end. In some embodiments, the needle assembly may include an introducer needle, which may include a sharp distal tip and a proximal end. In some embodiments, the needle assembly may include a needle hub affixed to the introducer needle and movably disposed in the barrel. In some embodiments, the needle assembly may include a spring disposed around the needle hub.

In some embodiments, the needle assembly may include a push button configured for selective engagement with the needle hub. In some embodiments, the push button may hold the needle hub against the bias of the spring. In some embodiments, the introducer needle may extend beyond the distal end of the barrel and through the catheter when the catheter adapter is adjacent to the distal end of the barrel. In some embodiments, the needle assembly may include a projection extending from the push button for engagement with the catheter adapter to prevent movement of the push button when the catheter adapter is adjacent to the distal end of the barrel. In some embodiments, the needle assembly may include a distally-extending arm contacting an inner surface of the barrel. In some embodiments, the distally-extending arm may be configured to drag along the inner surface of the barrel in response to depression of the push button and expansion of the spring.

In some embodiments, a distal end of the distally-extending arm may include a hook. In some embodiments, the distally-extending arm may be monolithically formed as a single unit with the spring. In some embodiments, the needle assembly may include a clip separate from the spring, and the clip may include the distally-extending arm. In some embodiments, the distally-extending arm may be a first distally-extending arm. In some embodiments, the needle assembly may include a second distally-extending arm opposite the first distally-extending arm. In some embodiments, the clip may include a coil. In some embodiments, a first end of the coil may include the first distally-extending arm, and a second end of the coil may include the second distally-extending arm. In some embodiments, a distal end of the first distally-extending arm may include a hook, and a distal end of the second distally-extending arm may include another hook.

A second set of embodiments is now described. In some embodiments, a catheter system may include a catheter assembly, which may include a catheter adapter. In some embodiments, the catheter adapter may include a distal end, a proximal end, and a catheter adapter lumen extending through the distal end of the catheter adapter and the proximal end of the catheter adapter. In some embodiments, the catheter system may include a catheter extending from the distal end of the catheter adapter.

In some embodiments, the catheter system may include a needle assembly, which may include a barrel. In some embodiments, the barrel may include a proximal end, a distal end, and a side hole between the proximal end of the barrel and the distal end of the barrel. In some embodiments, the needle assembly may include an introducer needle, which may include a sharp distal tip and a proximal end. In some embodiments, the needle assembly may include a needle hub affixed to the introducer needle and movably disposed in the barrel. In some embodiments, the needle hub may include a distally-extending arm forming a push button within the side hole. In some embodiments, the push button may be configured for selective engagement with the barrel.

In some embodiments, the needle assembly may include a spring disposed around the needle hub. In some embodiments, when the push button is within the side hole, the push button may hold the needle hub against the bias of the spring. In some embodiments, in response to depression of the push button, the spring may be configured to expand to retract the introducer needle. In some embodiments, the distally-extending arm may be a first distally-extending arm. In some embodiments, the needle hub may include a second distally-extending arm opposite the first distally-extending arm. In some embodiments, the side hole may be a first side hole. In some embodiments, the barrel may include a second side hole opposite the first side hole, the second distally-extending arm forming another push button within the second side hole. In some embodiments, the other push button may be configured for selective engagement with the barrel. In some embodiments, in response to depression of the push button and the other push button, the spring may be configured to expand to retract the introducer needle. In some embodiments, the catheter system may include a vent plug at a proximal end of the needle hub.

A third set of embodiments is now described. In some embodiments, a catheter system may include a catheter assembly, which may include a catheter adapter. In some embodiments, the catheter adapter may include a distal end, a proximal end, and a catheter adapter lumen extending through the distal end of the catheter adapter and the proximal end of the catheter adapter. In some embodiments, the catheter assembly may include a catheter extending from the distal end of the catheter adapter. In some embodiments, the catheter system may include a needle assembly, which may include a telescopic barrel. In some embodiments, the telescopic barrel may include a main barrel and one or more inner sleeves nested within the main barrel. In some embodiments, the main barrel may include a side hole. In some embodiments, the inner sleeve may include a distally-extending arm forming a push button within the side hole. In some embodiments, the push button may be configured for selective engagement with the main barrel.

In some embodiments, the needle assembly may include an introducer needle, which may include a sharp distal tip and a proximal end. In some embodiments, the needle assembly may include a needle hub affixed to the introducer needle and coupled to the telescopic barrel. In some embodiments, the needle assembly may include a spring disposed around the needle hub. In some embodiments, when the push button is within the side hole, the push button may hold the needle hub against the bias of the spring.

In some embodiments, in response to depression of the push button, the spring may be configured to expand. In some embodiments, in response to the spring expanding, the telescopic barrel may expand and the introducer needle may be retracted into the telescopic barrel. In some embodiments, the push button may include a distal stop surface configured to contact a rim of the main barrel to prevent collapsing of the telescopic barrel after the telescopic barrel expands and the introducer needle is retracted into the telescopic barrel. In some embodiments, the distal stop surface may be perpendicular to a longitudinal axis of the telescopic barrel. In some embodiments, the catheter system may include a vent plug at a proximal end of the telescopic barrel.

A fourth set of embodiments is now described. In some embodiments, a catheter system may include a catheter assembly, which may include a catheter adapter. In some embodiments, the catheter adapter may include a distal end, a proximal end, and a catheter adapter lumen extending through the distal end of the catheter adapter and the proximal end of the catheter adapter. In some embodiments, the catheter assembly may include a catheter extending from the distal end of the catheter adapter.

In some embodiments, the catheter assembly may include a needle assembly. In some embodiments, the needle assembly may include a barrel, which may include a proximal end, a distal end, and a side hole between the proximal end of the barrel and the distal end of the barrel. In some embodiments, the introducer needle may extend beyond the distal end of the barrel and through the catheter.

In some embodiments, the needle assembly may include an introducer needle, which may include a sharp distal tip and a proximal end. In some embodiments, the needle assembly may include a needle hub affixed to the introducer needle. In some embodiments, the needle hub may include a flexible extension disposed within the side hole and holding the needle hub against the bias of the spring. In some embodiments, the needle assembly may include a spring disposed around the needle hub.

In some embodiments, the needle assembly may include a lever arm coupled to the barrel and aligned with the side hole in the barrel. In some embodiments, in response to depression of the lever arm into the side hole, the lever arm may release the flexible extension from the side hole and the spring may expand. In some embodiments, in response to the expanding of the spring, the needle hub may be moved proximally and the introducer needle may be retracted.

In some embodiments, the needle hub may include another flexible extension opposite the flexible extension. In some embodiments, the other flexible extension may be configured to drag along the inner surface of the barrel in response to the expanding of the spring. In some embodiments, a proximal end of the lever arm may include a protrusion. In some embodiments, the flexible extension may be configured to drag along the inner surface of the barrel in response to the expanding of the spring.

It is to be understood that both the foregoing general description and the following detailed description are examples and explanatory and are not restrictive of the invention, as claimed. It should be understood that the various embodiments are not limited to the arrangements and instrumentality illustrated in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

DESCRIPTION OF EMBODIMENTS

Figure 1:
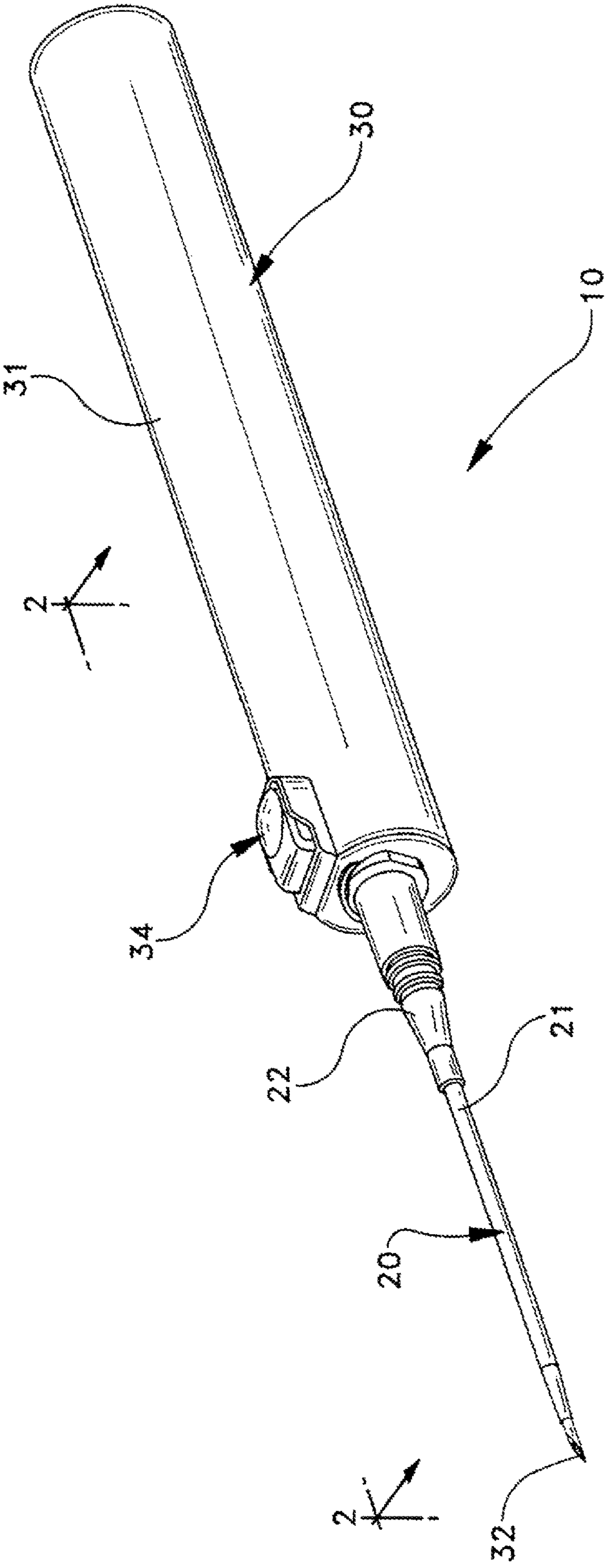
FIG. 1 (Prior Art)
FIG. 1 is an upper perspective view of a prior art catheter system.
Figure 2:
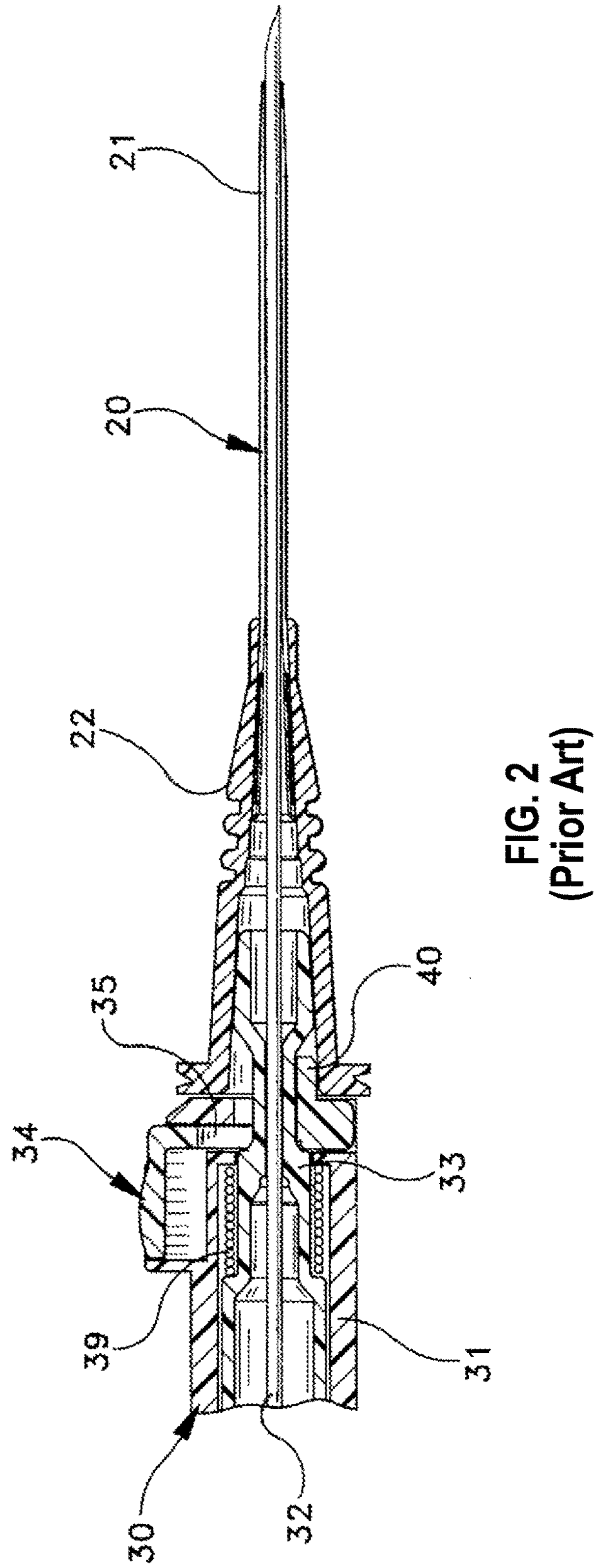
FIG. 2 (Prior Art)
FIG. 2 is a cross-section view taken along line 2-2 of FIG. 1 prior to activation of a spring mechanism.
Figure 3:
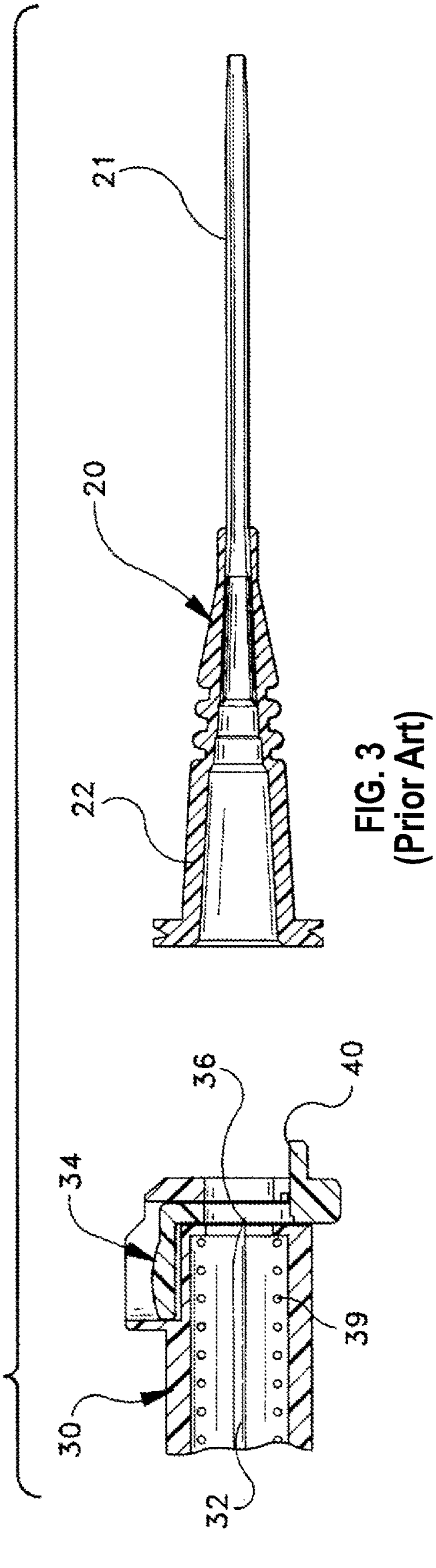
FIG. 3 (Prior Art)
FIG. 3 is a cross-sectional view of the prior art catheter system similar to the view shown in FIG. 2 but with the catheter advanced distally with respect to an introducer needle assembly, a spring activated, and a needle withdrawn into a barrel.
Figure 4:
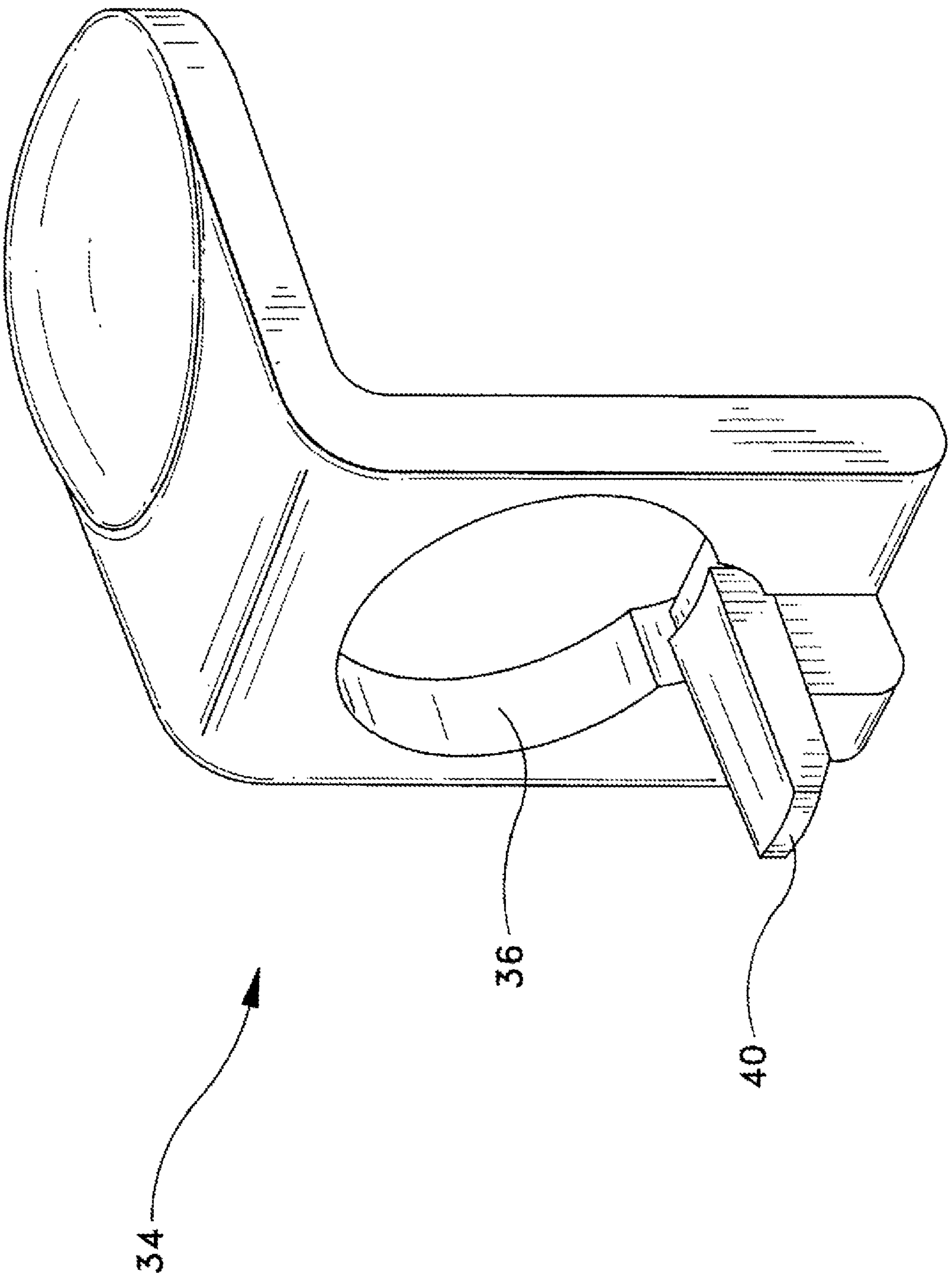
FIG. 4 (Prior Art)
FIG. 4 is an upper perspective view of a push button of the prior art catheter system.
Figure 5:
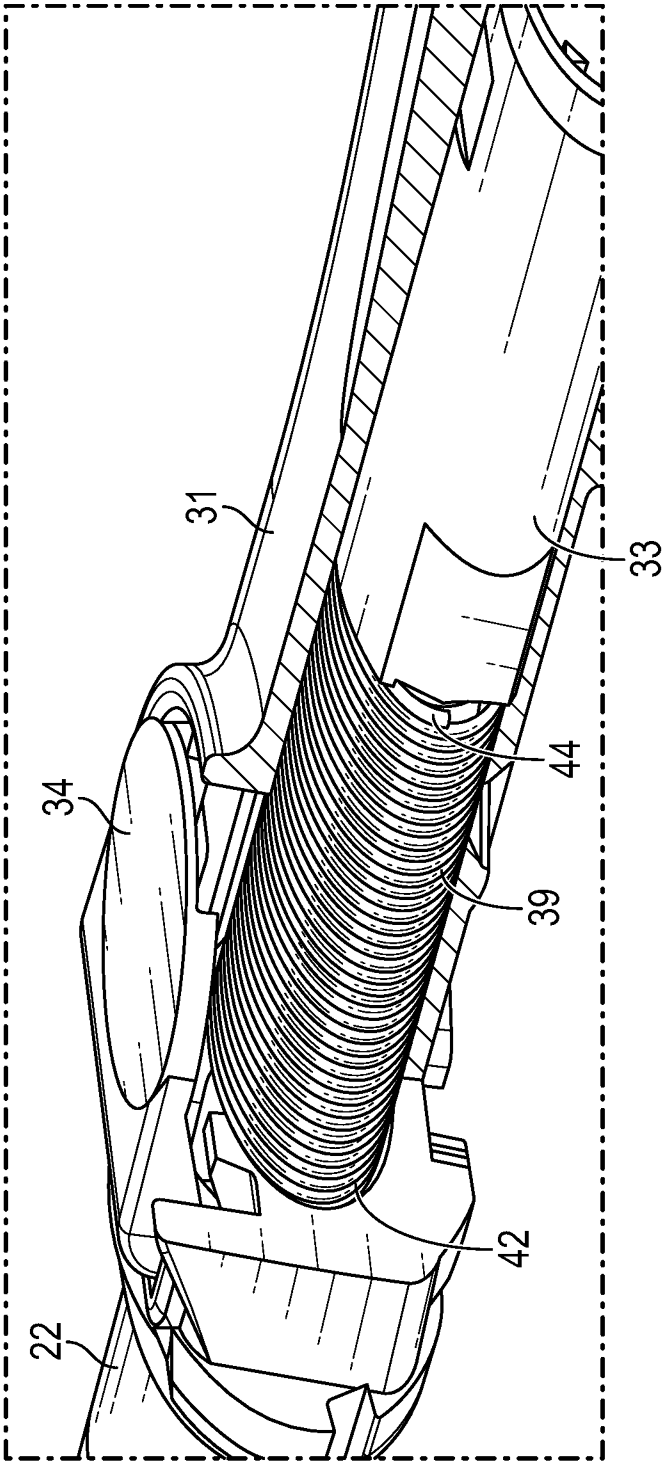
FIG. 5 (Prior Art)
FIG. 5 is a partial cutaway view of a portion of the prior art catheter system prior to activation of the spring mechanism, according to some embodiments.

Referring now to FIGS. 1-5, a prior art catheter system 10 is illustrated. A catheter 20 includes a tube 21 which is affixed to a catheter adapter 22. A needle assembly 30 includes a handle or barrel 31, an introducer needle 32, a carrier or needle hub 33, a spring 39, and an activation latch or push button 34. The spring 39 is located about the introducer needle 32 and the needle hub 33 and extends between the needle hub 33 and a distal end of barrel 31. The push button 34 extends into the barrel 31 via a slot 35 formed in the barrel 31 adjacent to the distal end. The push button 34 includes a keyhole shaped opening 36 that allows the introducer needle 32 and the needle hub 33 to extend through the push button 34. The push button 34 also includes a projection 40 that extends toward the distal end of catheter 20 and a distal end of the prior art catheter system 10.

When push button 34 is "up" in the non-activated position, a smaller portion of keyhole shaped opening 36 is in communication with a lumen of the barrel 31. In this position, the smaller opening engages the needle hub 33 and holds the needle hub 33 adjacent to the distal end of barrel 31 against the force of the spring 39. The needle hub 33 has a generally hour-glass shape so that its medial portion has a smaller diameter than either end. This shape facilitates engagement between the smaller opening in keyhole shaped opening 36 of the push button 34 and the needle hub 33. When the push button 34 is in the non-activated position, the projection 40 is located inside the catheter adapter 22. Thus, when the catheter 20 is still located on the introducer needle 32 with the catheter adapter 22 adjacent to the distal end of the barrel 31, the projection 40 prevents the push button 34 from being moved "down" into the activated position. The projection 40 generally has a length of between about 0.5 mm and about 2.5 mm. The length used should be long enough so projection 40 engages the catheter adapter 22 when the catheter adapter 22 is adjacent to the distal end of barrel 31. However, the projection 40 should not be so long that it interferes with the use of the catheter 20 and the introducer needle 32.

When the catheter 20 is moved off the introducer needle 32 so the catheter adapter 22 is not adjacent to the distal end of the barrel 31, the push button 34 can be depressed or moved "down," i.e. activated, because the catheter adapter 22 no longer interferes with the movement of the projection 40. In this position, the larger opening of the keyhole shaped opening 36 no longer engages the needle hub 33. The larger opening of the keyhole shaped opening 36 should be larger than the maximum diameter of the needle hub 33. The spring 39 can thus force the needle hub 33 to the proximal end of the barrel 31 and withdraw the sharp distal tip of the introducer needle 32 into the barrel 31.

The projection 40 on the push button 34 can also be angled. This configuration allows a clinician to activate the push button 34 by pressing down firmly on the push button 34. This downward force will transmit some axial force to the catheter adapter 22 because of a wedge shape of the projection. The catheter adapter 22 will then be advanced in the distal direction clearing the way for complete depression of push button 34. The wedge may be at an angle of between about 15 degrees and about 25 degrees to the longitudinal axis of catheter adapter 22. In some embodiments, the push button 34 of the prior art catheter system 10 may operate similar to the activation latch described in U.S. Pat. No. 5,501,675, filed Dec. 27, 1994, entitled "SAFETY CATHETER ASSEMBLY HAVING SAFETY STOP PUSH BUTTON", which is hereby incorporated by reference in its entirety.

The spring 39 of the prior art catheter system 10 is uniformly tapered inwardly from a distal end 42 to a proximal end 44 of the spring 39. Thus, an outer diameter and an inner diameter of the spring 39 at the distal end 42 may be greater than an outer diameter and an inner diameter, respectively, of the spring 39 at the proximal end 44. The spring 39 that is uniformly tapered inwardly may contribute to blood splatter when the push button 34 is depressed and the spring 39 expands to force the needle hub 33 to the proximal end of the barrel 31.

Figure 6A:
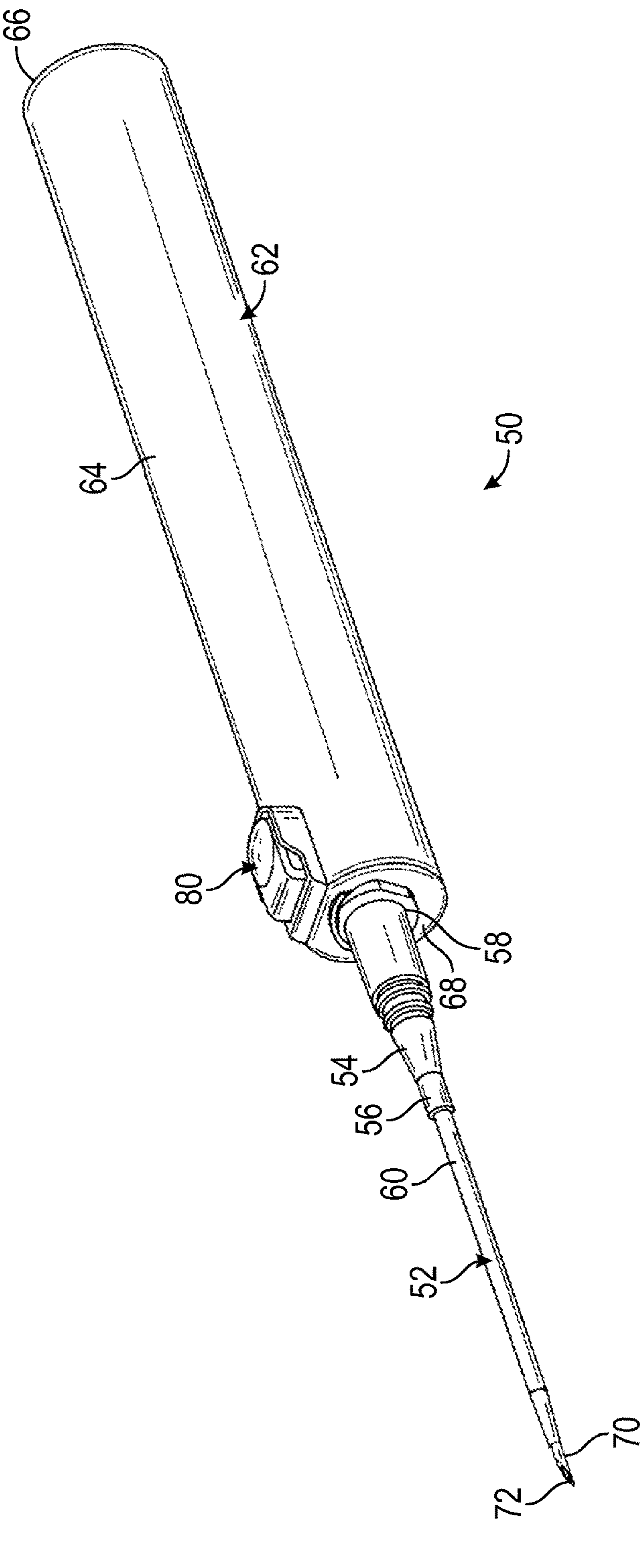
FIG. 6A is an upper perspective view of an example catheter system, according to some embodiments.
Figure 6B:
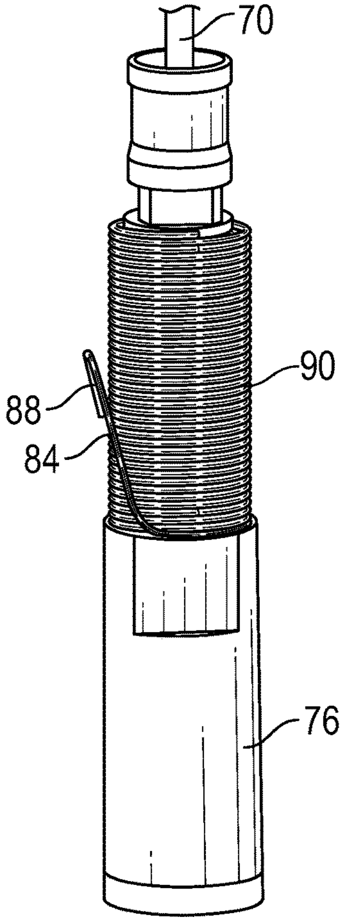
FIG. 6B is an upper perspective view of an example needle assembly of the catheter system of FIG. 6A, according to some embodiments.
Figure 6C:
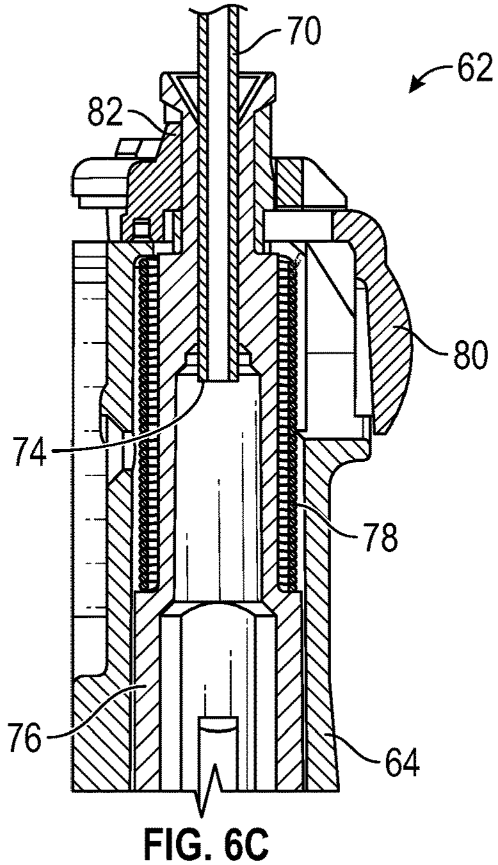
FIG. 6C is a cross-sectional view of a portion of the catheter system of FIG. 6A prior to activation of an example push button and expansion of an example spring, according to some embodiments.
Figure 6D:
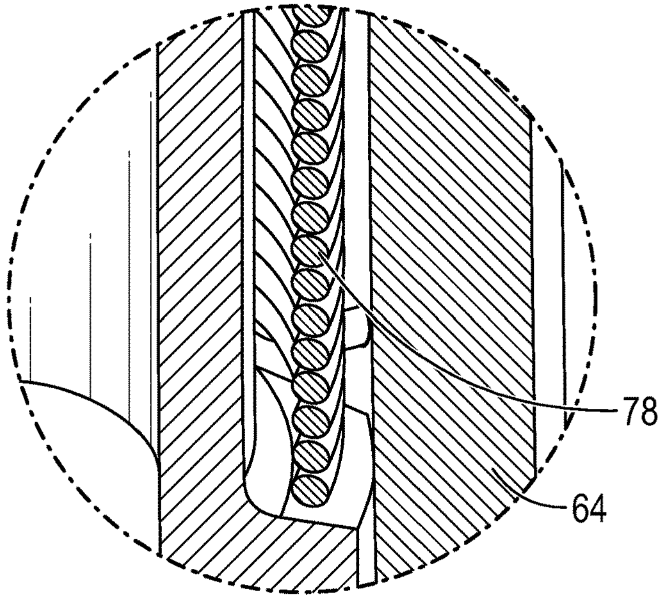
FIG. 6D is an enlarged cross-sectional view of a portion of FIG. 6C, according to some embodiments.

Referring now to FIGS. 6A-6C, in some embodiments, a catheter system 50 may include a catheter assembly 52, which may include a catheter adapter 54. In some embodiments, the catheter adapter 54 may include a distal end 56, a proximal end 58, and a catheter adapter lumen extending through the distal end 56 of the catheter adapter 54 and the proximal end 58 of the catheter adapter 54. In some embodiments, the catheter system 50 may include a catheter 60 extending from the distal end 56 of the catheter adapter 54.

In some embodiments, the catheter system 50 may include a needle assembly 62, which may include a barrel 64. In some embodiments, the barrel 54 may act as a grip for a user. In some embodiments, the barrel 64 may include a proximal end 66 and a distal end 68. In some embodiments, the needle assembly 62 may include an introducer needle 70, which may include a sharp distal tip 72 and a proximal end 74. In some embodiments, the needle assembly 62 may include a needle hub 76 affixed to the introducer needle 70 and movably disposed in the barrel 64. In some embodiments, the needle assembly 62 may include a spring 78 disposed around the needle hub 76.

In some embodiments, the needle assembly 62 may include a push button 80 configured for selective engagement with the needle hub 76. In some embodiments, the push button 80 may hold the needle hub 76 against the bias of the spring 78, which may be compressed. In some embodiments, the introducer needle 70 may extend beyond the distal end 68 of the barrel 64 and through the catheter 60 when the catheter adapter 54 is adjacent to the distal end 68 of the barrel 64. In some embodiments, the needle assembly 62 may include a projection 82 extending from the push button 80 for engagement with the catheter adapter 54 to prevent movement or depression of the push button 80 when the catheter adapter 54 is adjacent to the distal end 68 of the barrel 64.

In some embodiments, the needle assembly 62 may include a distally-extending arm 84 contacting an inner surface 86 of the barrel 64. In some embodiments, the distally-extending arm 84 may be configured to drag along the inner surface 86 of the barrel 64 in response to depression of the push button 80 and expansion of the spring 78. In some embodiments, the distal end of the distally-extending arm 84 may drag along the inner surface 86 of the barrel 64 along an entire distance the distal end of the distally-extending arm 84 moves after depression of the push button 80 and during expansion of the spring 78 to withdraw the introducer needle 70.

In some embodiments, a distal end of the distally-extending arm 84 may include a hook 88, which may increase friction between the distally-extending arm 84 and the inner surface 86 of the barrel 64. In some embodiments, the distally-extending arm 84 may create friction between the inner surface 86 and the spring 78, which may decrease a speed of the needle hub 76 when the spring 78 expands and the introducer needle 70 is withdrawn. The decrease in the speed of the needle hub 76 may prevent blood from splattering during withdrawal of the needle hub 76. In some embodiments, due to the decrease in the speed of the needle hub 76 when the introducer needle 70 is withdrawn, the catheter system 50 may not include a septum within the barrel 64 and/or may not include silicon gel or a similar gel. In some embodiments, the distally-extending arm 84 may extend across a clearance or space between a coil portion 90 of the spring and the inner surface 86 of the barrel 64.

In some embodiments, the catheter system 50 may be similar or identical to the prior art catheter system 10 of FIGS. 1-5 in terms of one or more features and/or operation. For example, FIG. 6A-6D illustrate the push button 80, the needle hub 76, and the barrel 64, which may be similar or identical to the push button 34, the needle hub 33, and the barrel 31, respectively, of the prior art catheter system 10 of FIGS. 1-5 in terms of one or more features and/or operation, according to some embodiments.

Figure 7C:
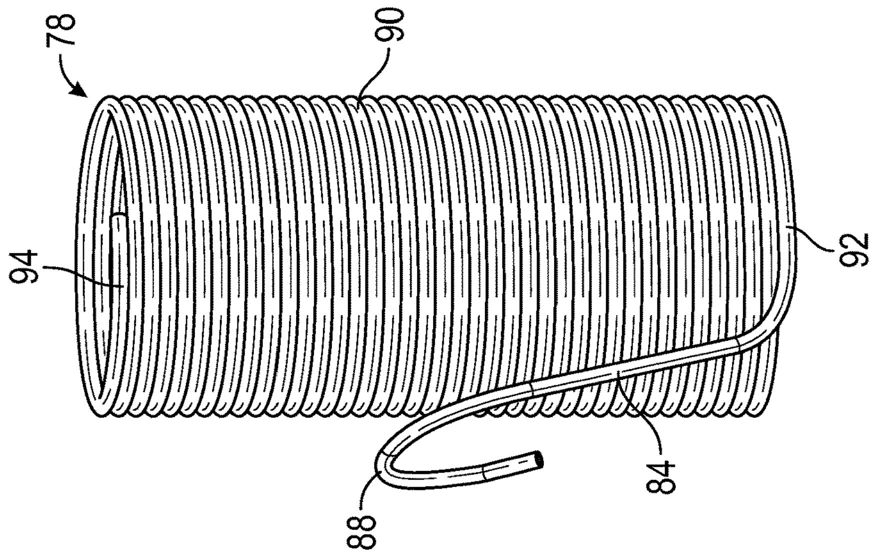
FIG. 7C is an upper perspective view of the spring, illustrating another example distally-extending arm, according to some embodiments.
Figure 7B:
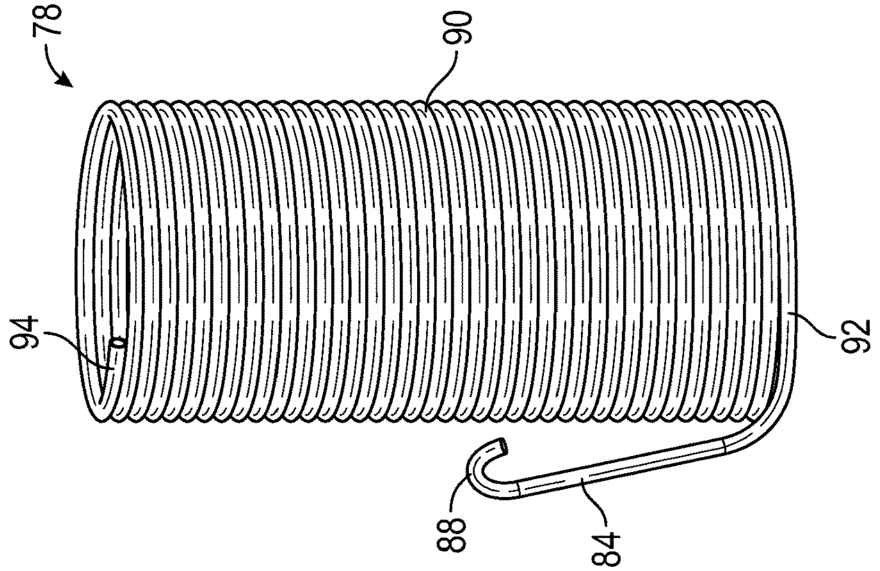
FIG. 7B is an upper perspective view of the spring, illustrating another example distally-extending arm, according to some embodiments.
Figure 7A:
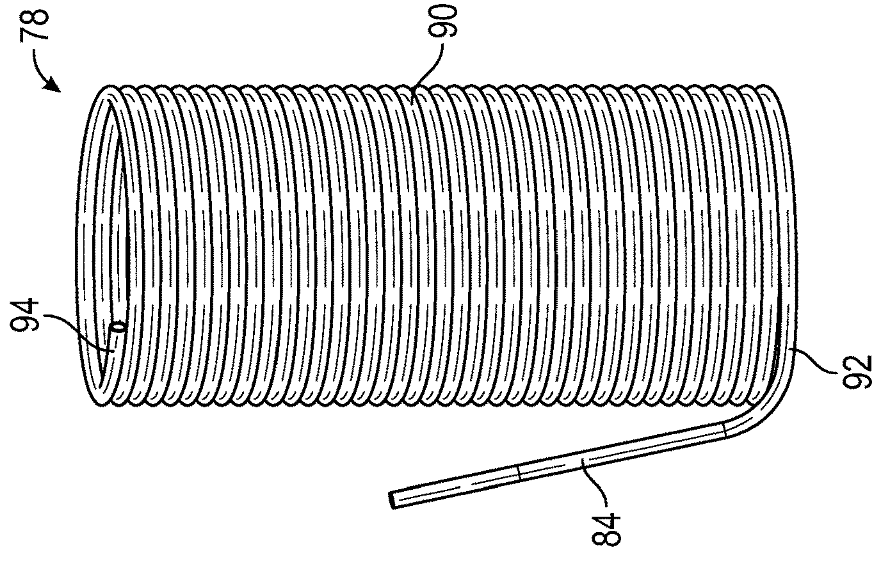
FIG. 7A is an upper perspective view of an example spring, illustrating an example distally-extending arm, according to some embodiments.
Figure 7D:
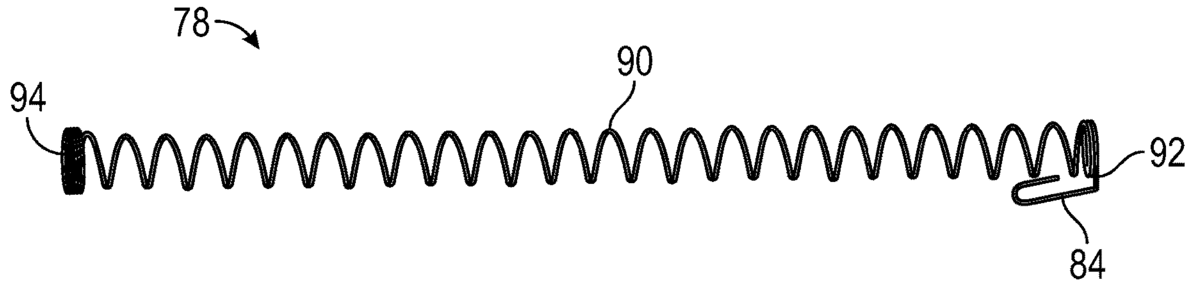
FIG. 7D is an upper perspective view of the spring, illustrating another example distally-extending arm and the spring in an expanded position after depression of a push button, according to some embodiments.
Figure 7E:
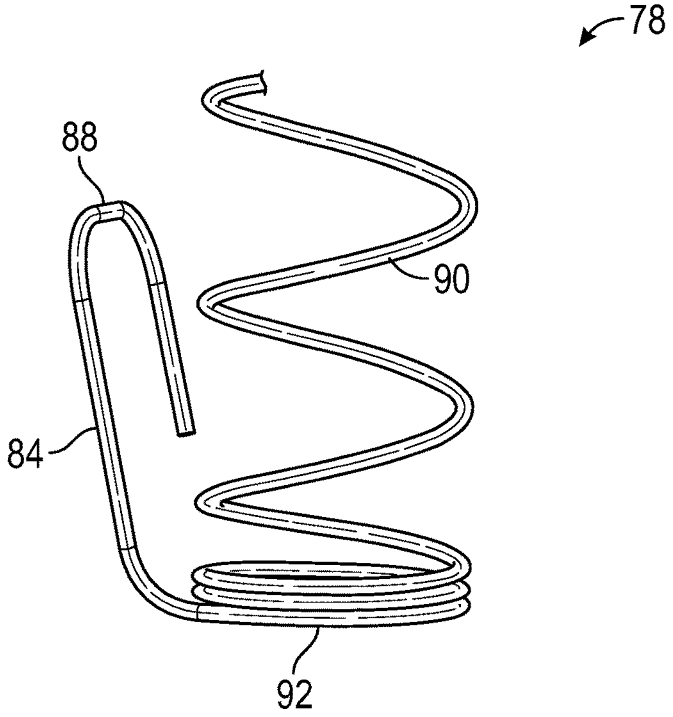
FIG. 7E is an enlarged upper perspective view of a proximal end of the spring with the distally-extending arm of FIG. 7D, according to some embodiments.
Figure 8D:
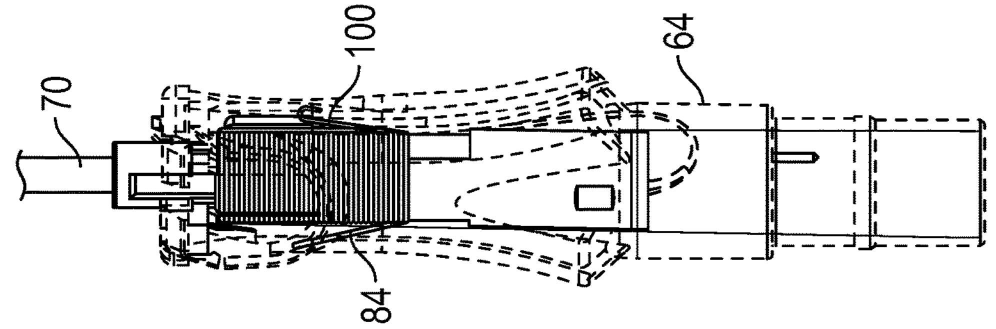
FIG. 8D is an upper perspective view of an example catheter system, according to some embodiments.
Figure 8C:
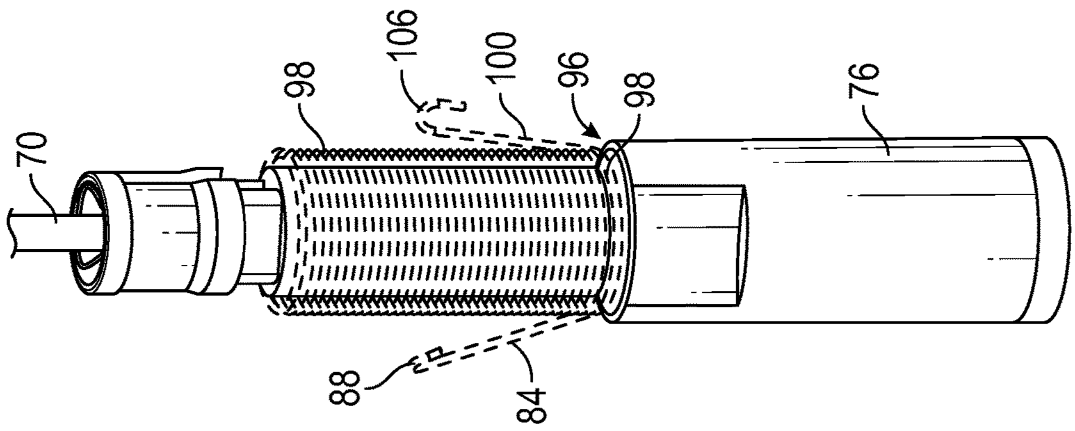
FIG. 8C is an upper perspective view of an example needle hub, illustrating an example clip, according to some embodiments.
Figure 8A:
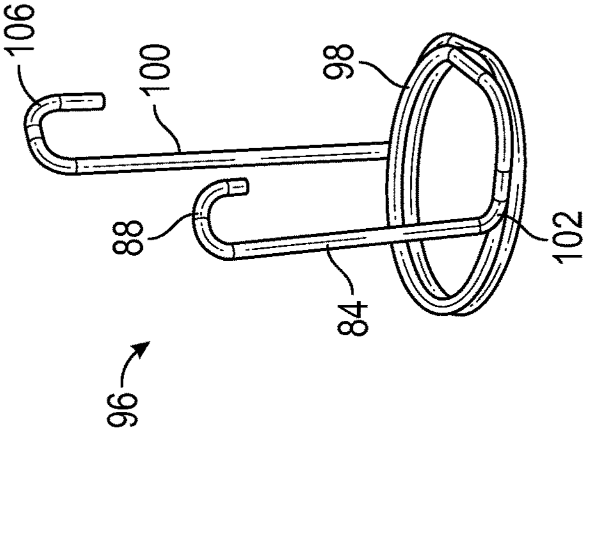
FIG. 8A is an upper perspective view of an example clip, according to some embodiments.
Figure 8B:
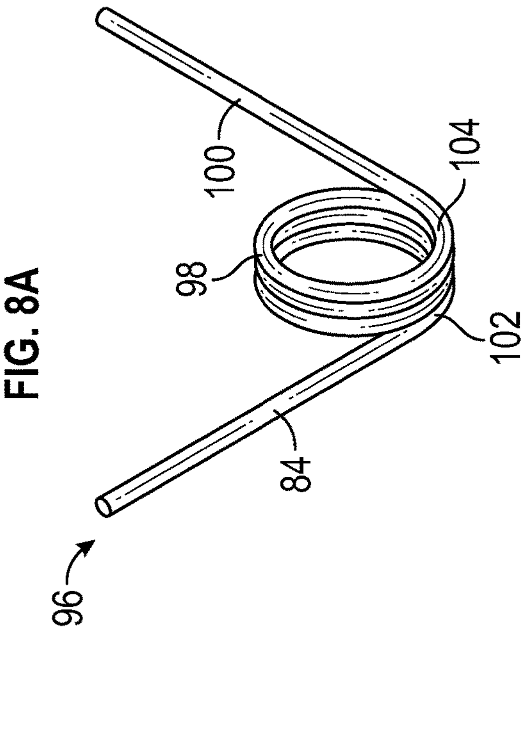
FIG. 8B is an upper perspective view of another example clip, according to some embodiments.
Figure 9A:
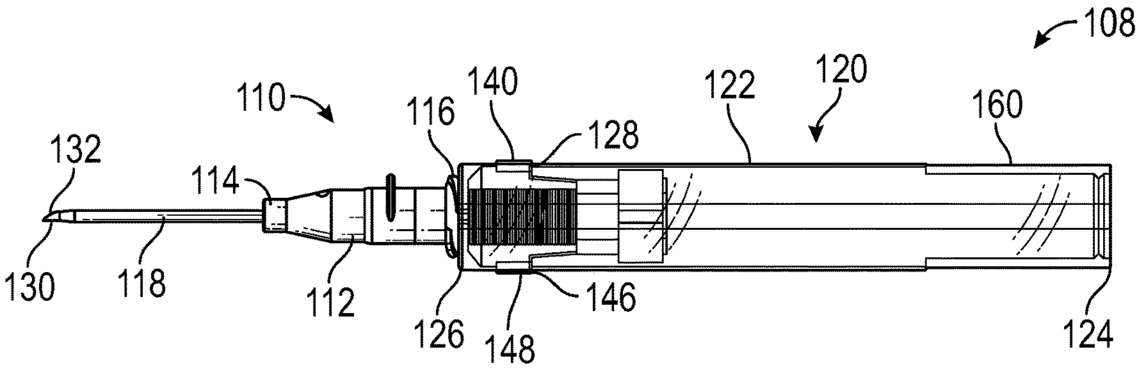
FIG. 9A is a side view of an example catheter system prior to expansion of an example spring, according to some embodiments.
Figure 9B:
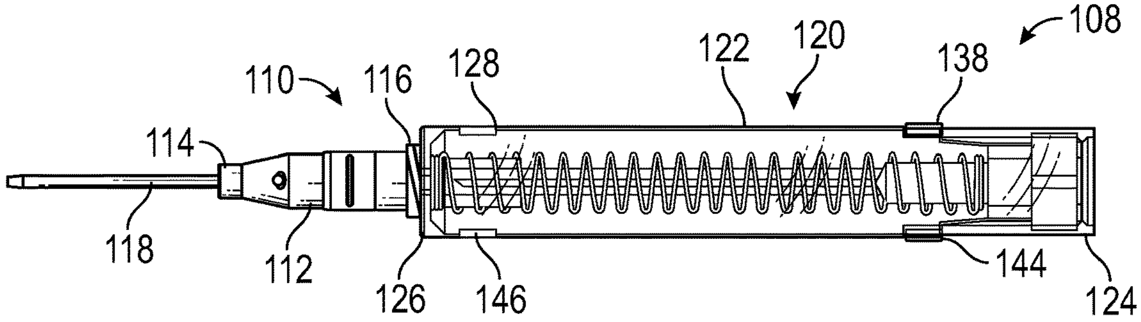
FIG. 9B is a top view of the catheter system of FIG. 9A after expansion of the spring, according to some embodiments.
Figure 9C:
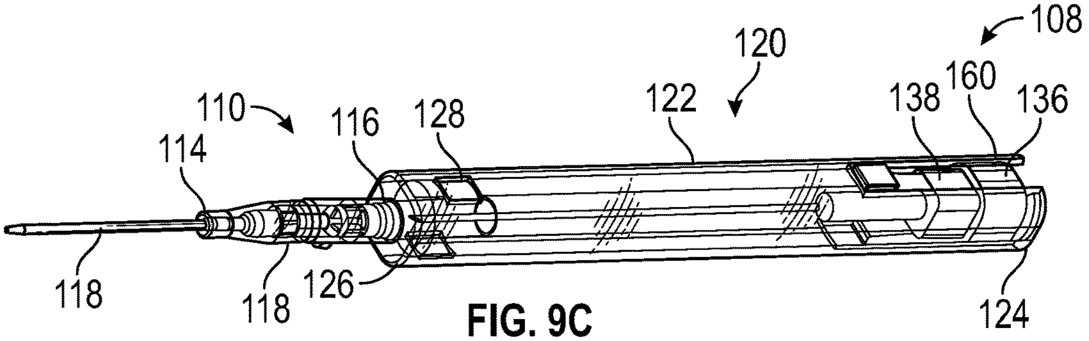
FIG. 9C is an upper perspective view of the catheter system of FIG. 9A after expansion of the spring, according to some embodiments.
Figure 9D:
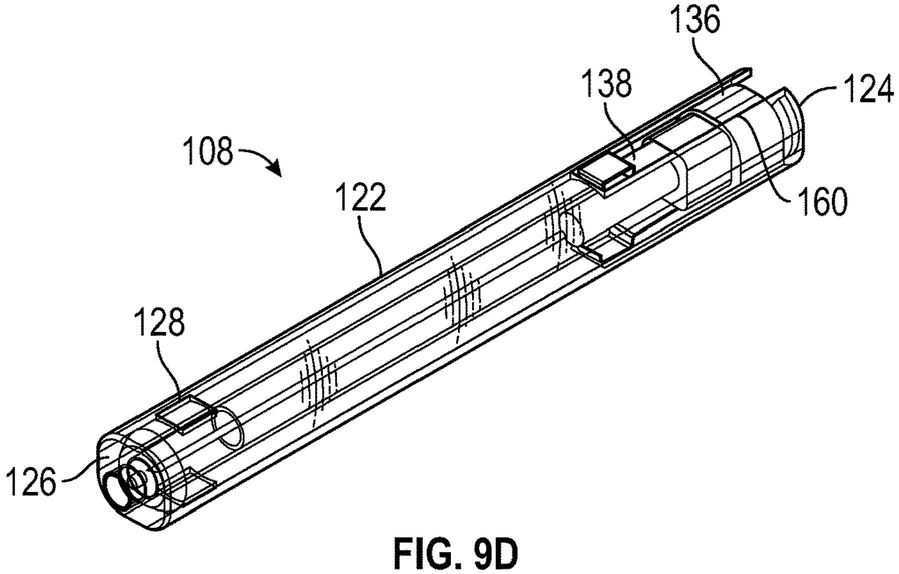
FIG. 9D is an upper perspective view of an example needle assembly of the catheter system of FIG. 9A after expansion of the spring, according to some embodiments.
Figure 10A:
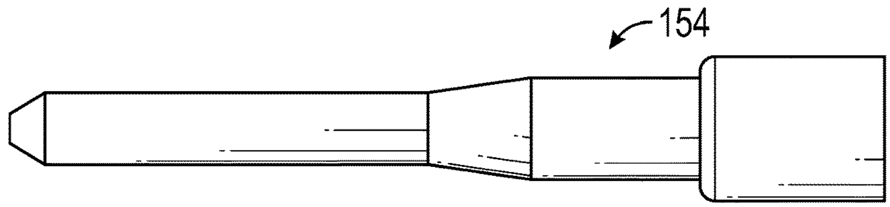
FIG. 10A is an upper perspective view of an example needle cover, according to some embodiments.
Figure 10B:
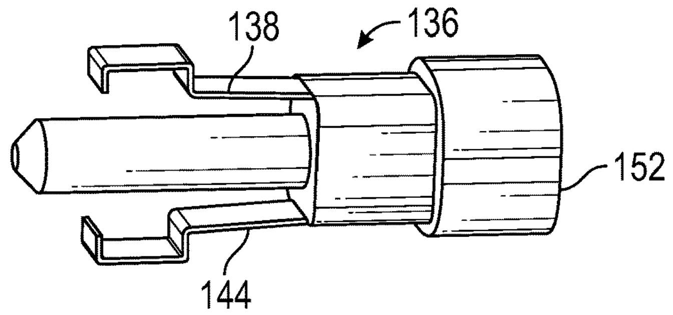
FIG. 10B is an upper perspective view of an example needle hub of the catheter system of FIG. 9A, according to some embodiments.
Figure 10C:
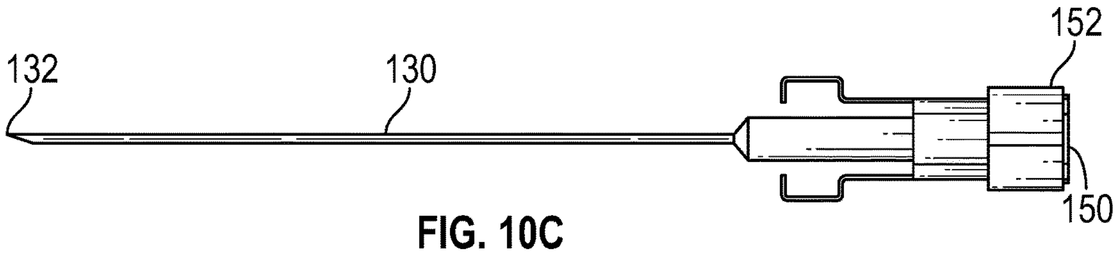
FIG. 10C is a side view of the needle hub and example introducer needle coupled to the needle hub, according to some embodiments.
Figure 10D:
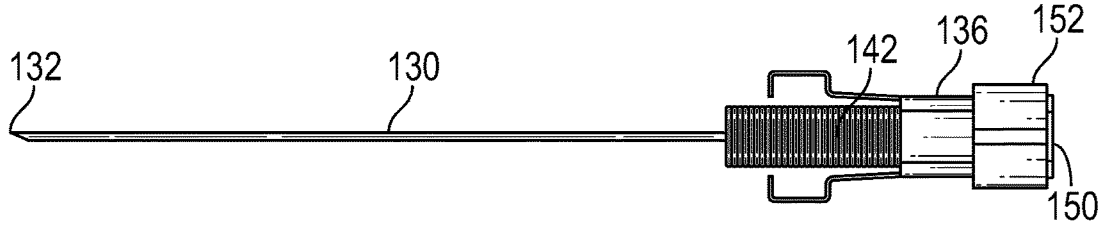
FIG. 10D is a side view of the spring surrounding the needle hub, illustrating the spring compressed and prior to expansion, according to some embodiments.
Figure 10E:
FIG. 10E is a cross-sectional view of the spring surrounding the needle hub, illustrating the spring compression and prior to expansion, according to some embodiments.
Figure 10F:
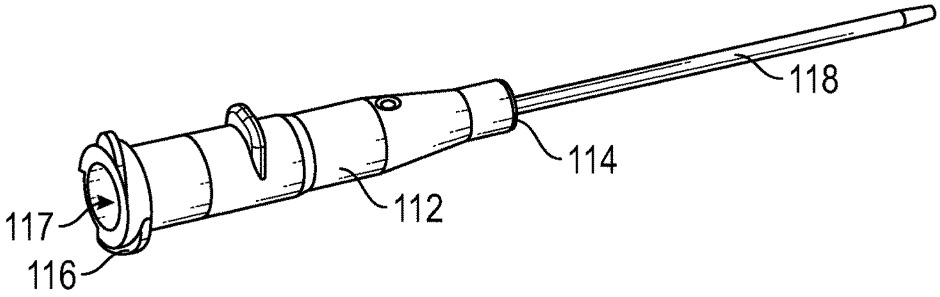
FIG. 10F is an upper perspective view of an example catheter assembly, according to some embodiments.
Figure 10G:
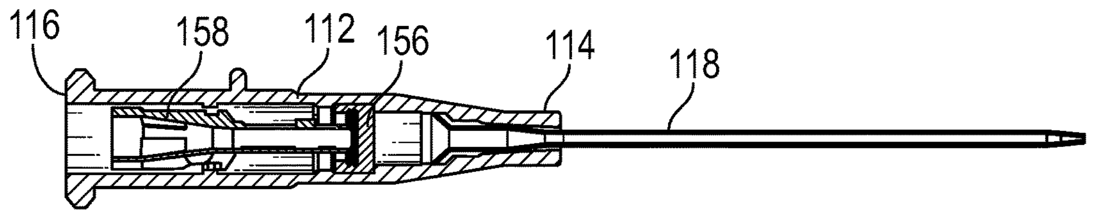
FIG. 10G is a cross-sectional view of the catheter assembly of FIG. 10F, according to some embodiments.
Figure 10H:
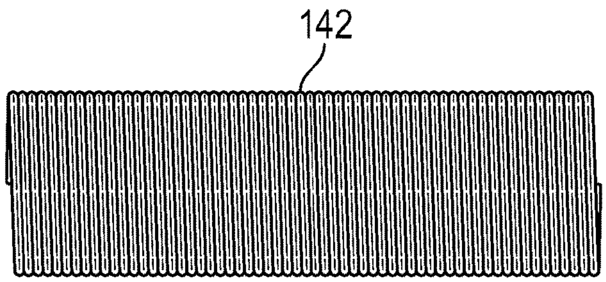
FIG. 10H is a side view of the spring in a compressed state, according to some embodiments.
Figure 10I:
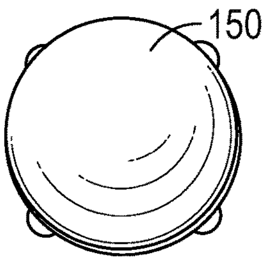
FIG. 10I is an upper perspective view of an example vent plug, according to some embodiments.
Figure 10J:
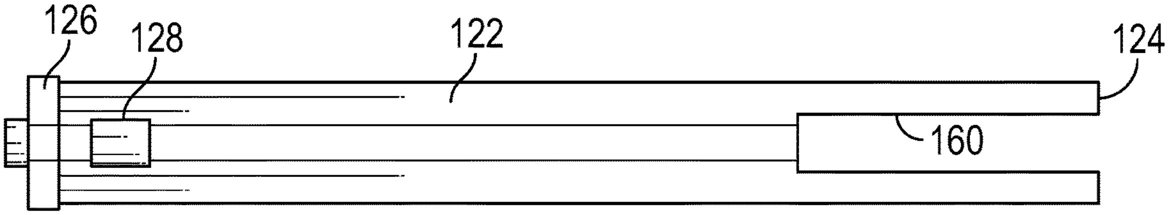
FIG. 10J is a top view of an example barrel of the needle assembly of the catheter system of FIG. 9A, according to some embodiments.
Figure 11A:
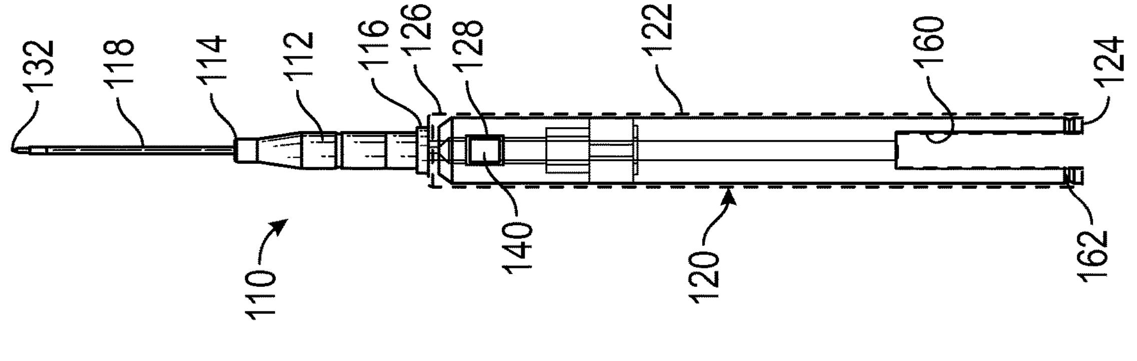
FIG. 11A is a top view of the catheter system of FIG. 9A prior to expansion of an example spring, according to some embodiments.
Figure 11B:
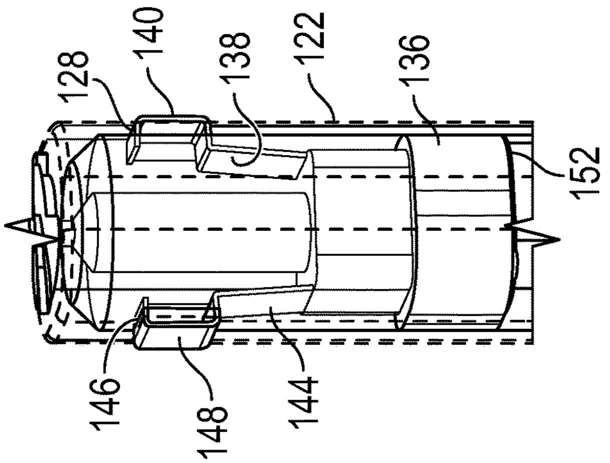
FIG. 11B is an upper perspective view of a portion of the catheter system of FIG. 9A prior to expansion of the spring, according to some embodiments.
Figure 11C:
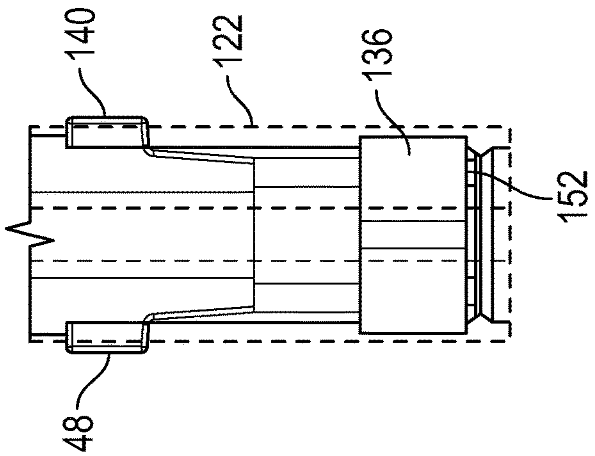
FIG. 11C is a top view of a portion of the catheter system of FIG. 9A prior to expansion of the spring, according to some embodiments.
Figure 11D:
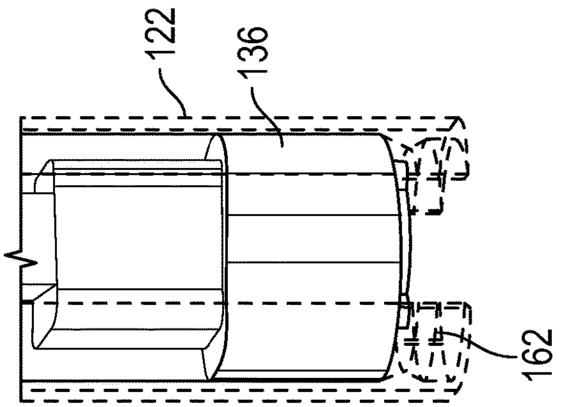
FIG. 11D is an upper perspective view of a portion of the catheter system of FIG. 9A prior to expansion of the spring, according to some embodiments.
Figure 12A:
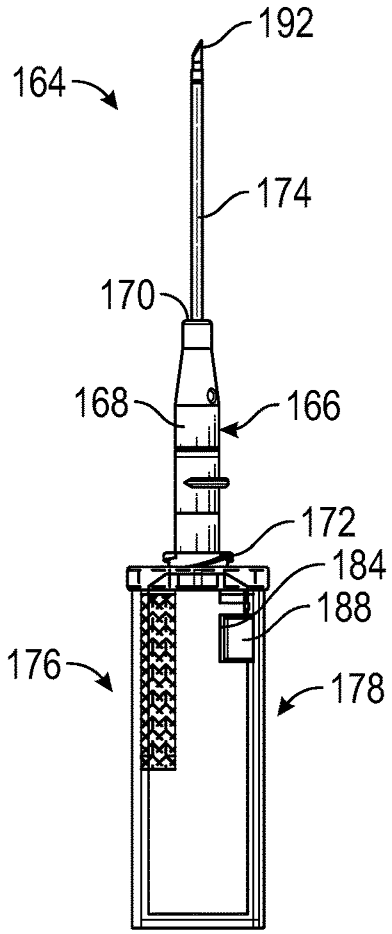
FIG. 12A is an upper perspective view of an example catheter system, illustrating an example telescopic barrel having an example first inner sleeve and an example second inner sleeve nested in an example main barrel, according to some embodiments.
Figure 12B:
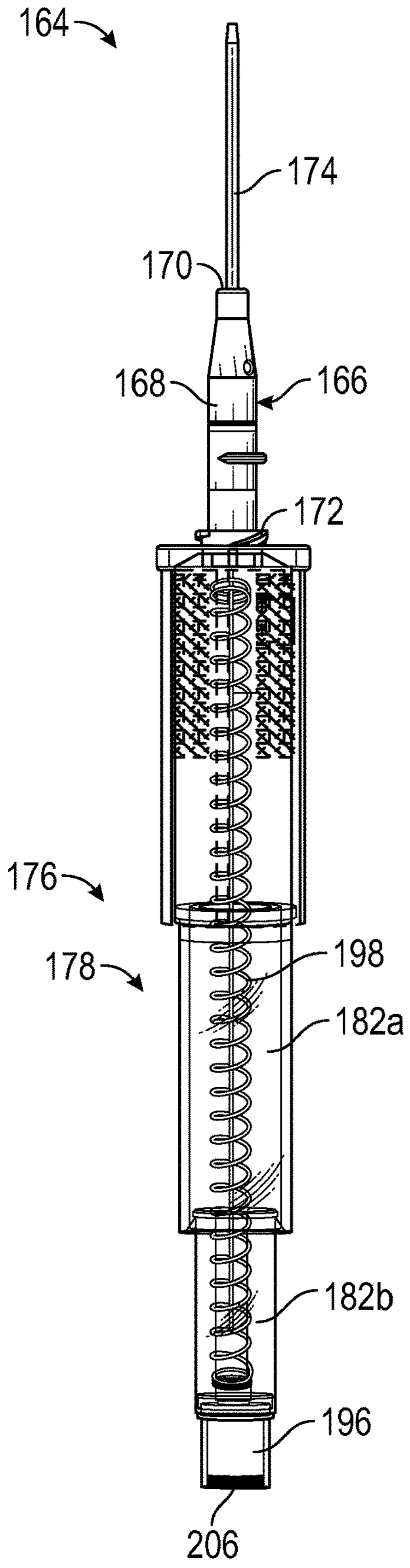
FIG. 12B is an upper perspective view of the catheter system of FIG. 12A, illustrating the telescopic barrel in an expanded position, according to some embodiments.
Figure 12C:
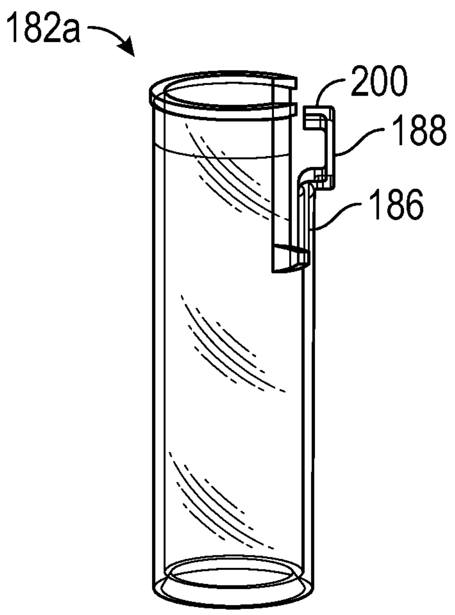
FIG. 12C is an upper perspective view of the first inner sleeve, according to some embodiments.
Figure 12D:
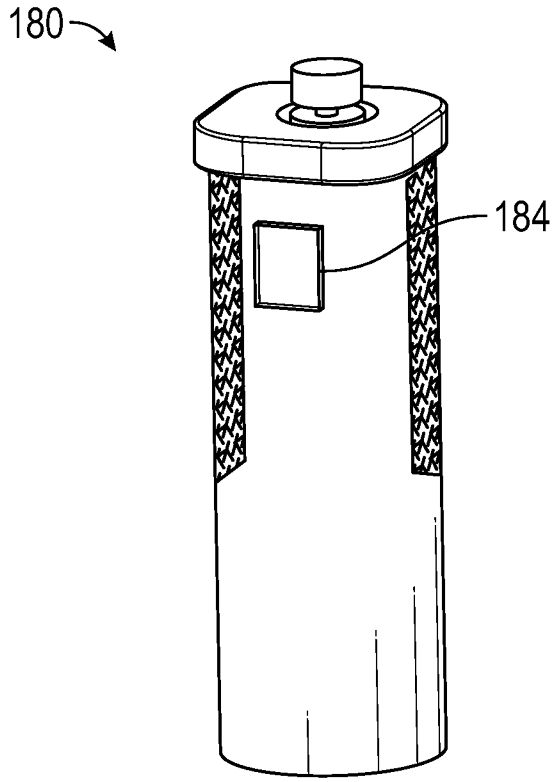
FIG. 12D is an upper perspective view of the main barrel, according to some embodiments.
Figure 12E:
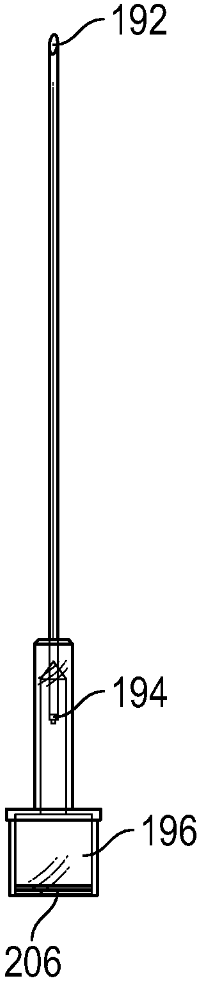
FIG. 12E is an upper perspective view of an example needle hub and example introducer needle, according to some embodiments.
Figure 12F:
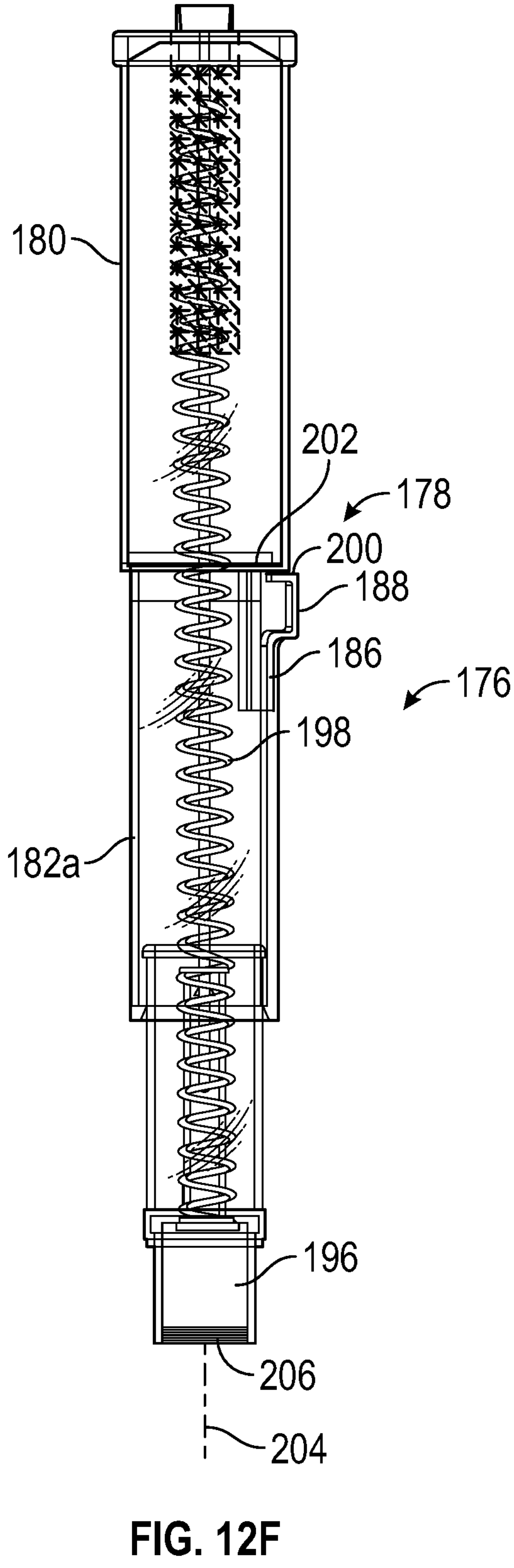
FIG. 12F is an upper perspective view of an example needle assembly of the catheter system of FIG. 12A, illustrating the telescopic barrel in an expanded position, according to some embodiments.
Figure 13A:
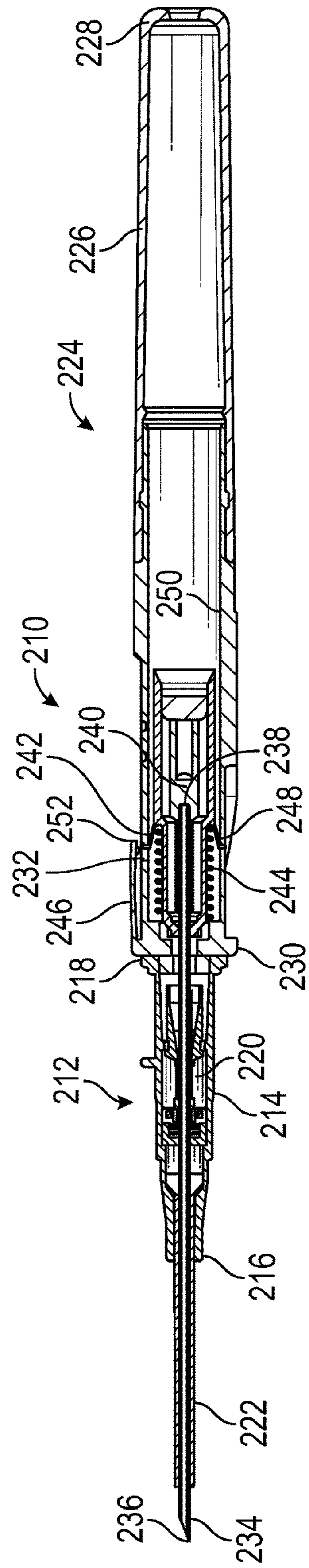
FIG. 13A is an upper perspective view of an example catheter system, illustrating an example flexible extension inserted into an example side hole of an example barrel to prevent expansion of an example spring and retraction of an example introducer needle, according to some embodiments.
Figure 13C:
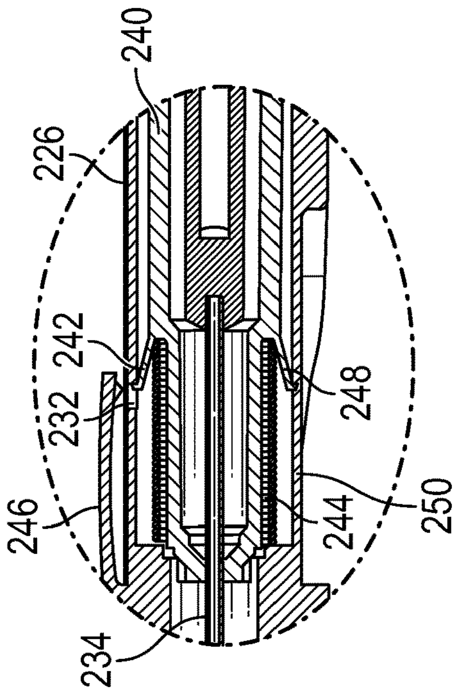
FIG. 13C is a cross-sectional view of the catheter system of FIG. 13A, illustrating the flexible extension inserted into the side hole of the barrel to prevent expansion of an example spring and retraction of the introducer needle, according to some embodiments.
Figure 13B:
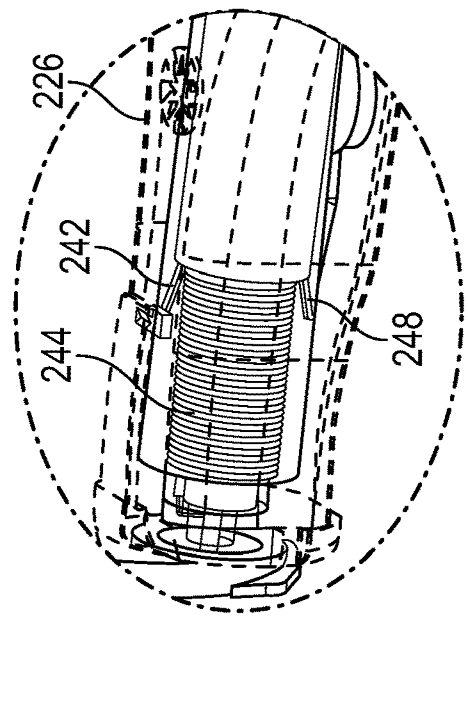
FIG. 13B is an upper perspective view of the catheter system of FIG. 13A, illustrating the flexible extension inserted into the side hole of the barrel to prevent expansion of an example spring and retraction of the introducer needle, according to some embodiments.
Figure 13F:
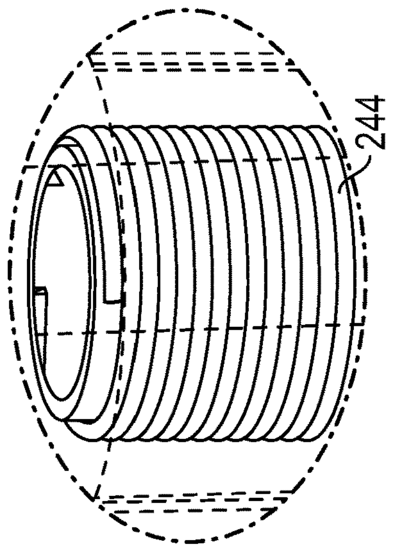
FIG. 13F is an upper perspective view of the spring of the catheter system of FIG. 13A in a compressed state, according to some embodiments.
Figure 13E:
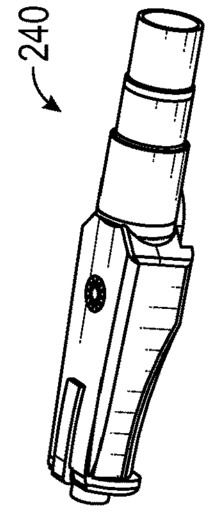
FIG. 13E is an upper perspective view of an example needle hub of the catheter system of FIG. 13A, according to some embodiments.
Figure 13D:
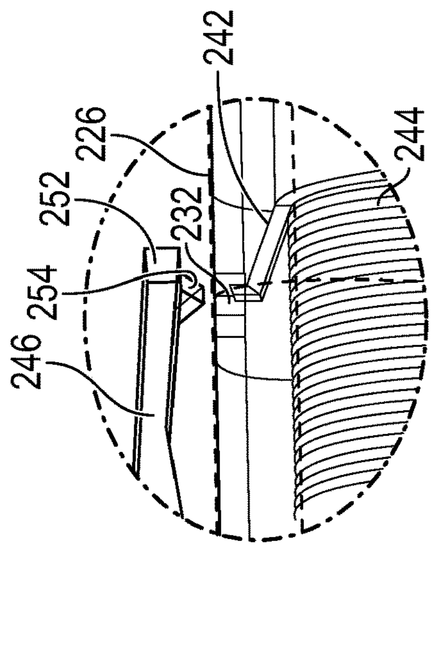
FIG. 13D is an enlarged upper perspective view of a portion of the catheter system of FIG. 13A, illustrating the flexible extension inserted into the side hole of the barrel to prevent expansion of an example spring and retraction of the introducer needle, according to some embodiments.

Referring now to FIGS. 7A-7C, in some embodiments, the distally-extending arm 84 may be coupled to the coil portion 90 of the spring 78 such that the distally-extending arm 84 moves with the spring 78. In some embodiments, the distally-extending arm 84 may be monolithically formed as a single unit with the spring 78, as illustrated in FIGS. 7A-7E. In some embodiments, the distally-extending arm 84 may be disposed at a proximal end of the spring 78 and/or proximate a proximal end 92 of the coil portion 90 of the spring 78, which may be include one or more turns of the coil portion 90 that are non-separating to support the distally-extending arm 84. In some embodiments, a distal end 94 of the coil portion 90 may include one or more turns of the coil portion 90 that are non-separating to support the spring 78 against the barrel 64 when the spring 78 expands, as illustrated, for example, in FIG. 7D. In some embodiments, the distal end of the distally-extending arm 84 may include the hook 88. In other embodiments, the distally-extending arm 84 may be generally straight, as illustrated, for example, in FIG. 7A. In some embodiments, a size and/or a direction of the hook 88 may vary according to, for example, a desired amount of friction, as illustrated in FIGS. 7B-7D.

Referring now to FIGS. 8A-8D, in some embodiments, the needle assembly 62 may include a clip 96 separate from the spring 78. In further detail, in some embodiments, the clip 96 may be a separate piece from the spring 78. In some embodiments, the clip 96 may include the distally-extending arm 84. In some embodiments, the clip 96 may be coupled to the spring 78 such that the distally-extending arm 84 moves with the spring 78. In some embodiments, the distally-extending arm 84 may be coupled to and/or extend from a coil 98 of the clip 96.

In some embodiments, the distally-extending arm 84 may be a first distally-extending arm. In some embodiments, the needle assembly 62 may include a second distally-extending arm 100, which may be opposite the first distally-extending arm. In some embodiments, a first end 102 of the coil 98 may include the first distally-extending arm, and a second end 104 of the coil 98 may include the second distally-extending arm 100. In some embodiments, a distal end of the first distally-extending arm may include the hook 88, and/or a distal end of the second distally-extending arm 100 may include another hook 106.

In some embodiments, the first distally-extending arm and the second distally-extending arm 100 may be configured to drag along the inner surface 86 of the barrel 64 in response to depression of the push button 80 and expansion of the spring 78. In some embodiments, the first distally-extending arm and the second distally-extending arm 100 may drag along the inner surface 86 of the barrel 64 along an entire distance the distal end of the distally-extending arm 84 moves after depression of the push button 80 and during expansion of the spring 78 to withdraw the introducer needle 70. In some embodiments, the first distally-extending arm and the second distally-extending arm 100 may create friction between the inner surface 86 and the spring 78, which may decrease a speed of the needle hub 76 when the spring 78 expands and the introducer needle 70 is withdrawn.

Referring now to FIGS. 9A-11D, in some embodiments, a catheter system 108 may include a catheter assembly 110, which may include a catheter adapter 112. In some embodiments, the catheter system 108 may be similar or identical to the prior art catheter system 10 of FIGS. 1-5 and/or the catheter system 50 of FIGS. 6-8 in terms of one or more features and/or operation. In some embodiments, the catheter adapter 112 may include a distal end 114, a proximal end 116, and a catheter adapter lumen 117 extending through the distal end 114 of the catheter adapter 112 and the proximal end 116 of the catheter adapter 112. In some embodiments, the catheter system 108 may include a catheter 118 extending from the distal end 114 of the catheter adapter 112.

In some embodiments, the catheter system 108 may include a needle assembly 120, which may include a barrel 122. In some embodiments, the barrel 122 may include a proximal end 124, a distal end 126, and a side hole 128 between the proximal end 124 of the barrel 122 and the distal end 126 of the barrel 122. In some embodiments, the needle assembly 120 may include an introducer needle 130, which may include a sharp distal tip 132 and a proximal end 134. In some embodiments, the needle assembly 120 may include a needle hub 136 affixed to the introducer needle 130 and movably disposed in the barrel 122.

In some embodiments, the needle hub 136 may include a distally-extending arm 138 forming a push button 140 within the side hole 128. In some embodiments, the push button 140 may be configured for selective engagement with the barrel 122. In some embodiments, the needle assembly 120 may include a spring 142 disposed around the needle hub 136. In some embodiments, when the push button 140 is within the side hole 128, the push button 140 may hold the needle hub 136 against the bias of the spring 142. In some embodiments, in response to depression of the push button 140, the spring 142 may be configured to expand to retract the introducer needle 130.

In some embodiments, the distally-extending arm 138 may be a first distally-extending arm. In some embodiments, the needle hub 136 may include a second distally-extending arm 144 opposite the first distally-extending arm, which may facilitate linear withdrawal of the needle hub 136. In some embodiments, the side hole 128 may be a first side hole. In some embodiments, the barrel 122 may include a second side hole 146 opposite the first side hole, the second distally-extending arm 144 forming another push button 148 within the second side hole. In some embodiments, the other push button 148 may be configured for selective engagement with the barrel 122. In some embodiments, in response to depression of the push button 140 and the other push button 148, the first distally-extending arm and the second distally-extending arm 144 may slide inside the shield as the spring 142 expands to retract the introducer needle 130. In some embodiments, the push button 140 within the side hole 128 and the other push button 148 within the second side hole 146 may prevent accidental activation or expansion of the spring 142.

In some embodiments, the catheter system 108 may include a vent plug 150 at a proximal end 152 of the needle hub 136. In some embodiments, the catheter system 108 may include a needle cover 154 configured to cover the sharp distal tip 132 when the introducer needle 130 is in an insertion configuration ready for insertion into a patient, such as illustrated, for example, in FIG. 9A. In some embodiments, the catheter adapter 112 may include a septum 156 and/or a septum actuator 158 configured to penetrate the septum 156 in response to insertion of a medical device into the proximal end 116 of the catheter adapter 112.

In some embodiments, a proximal end of the barrel 122 may include opposing slots 160 each configured to receive one of the distally-extending arm 138 and the second distally-extending arm 144. In some embodiments, the opposing slots 160 may allow the distally-extending arm 138 and the second distally-extending arm 144 to move outwardly after being biased inwardly against an inner surface of the barrel 122. In some embodiments, distal ends of each of the opposing slots 160 may act as a stop, contacting the distally-extending arm 138 and the second distally-extending arm 144 to prevent distal movement of the needle hub 136 after the introducer needle 130 is retracted within the barrel 122. In some embodiments, a bump 162 within a proximal end of the barrel 122 may act as a retention feature and hold the needle hub 136 within the barrel 122.

Referring now to FIGS. 12A-12F, in some embodiments, a catheter system 164 may include a catheter assembly 166, which may include a catheter adapter 168. In some embodiments, the catheter adapter 168 may include a distal end 170, a proximal end 172, and a catheter adapter lumen extending through the distal end 170 of the catheter adapter 168 and the proximal end 172 of the catheter adapter 168. In some embodiments, the catheter system 164 may be similar or identical to one or more of the prior art catheter system 10 of FIGS. 1-5, the catheter system 50 of FIGS. 6-8, and the catheter system 108 of FIGS. 9-11 in terms of one or more features and/or operation.

In some embodiments, the catheter assembly 166 may include a catheter 174 extending from the distal end 170 of the catheter adapter 168. In some embodiments, the catheter system 164 may include a needle assembly 176, which may include a telescopic barrel 178. In some embodiments, the telescopic barrel 178 may include a main barrel 180 and at least one inner sleeve 182 nested within the main barrel 180. In some embodiments, the main barrel 180 may include a side hole 184. In some embodiments, the inner sleeve 182 may include a distally-extending arm 186 forming a push button 188 within the side hole 184. In some embodiments, the push button 188 may be configured for selective engagement with the main barrel 180. In some embodiments, the inner sleeve 182 may be a first inner sleeve 182*a*, and the telescopic barrel 178 may include a second inner sleeve 182*b* that nests within the first inner sleeve and the main barrel 180, as illustrated, for example, in FIGS. 12A-12B. In some embodiments, friction between the main barrel 180 and the inner sleeve 182 may delay an initial acceleration of the needle hub 196, which may reduce blood splatter.

In some embodiments, the needle assembly 176 may include an introducer needle 190, which may include a sharp distal tip 192 and a proximal end 194. In some embodiments, the needle assembly 176 may include a needle hub 196 affixed to the introducer needle 190 and coupled to the telescopic barrel 178. In some embodiments, the needle assembly 176 may include a spring 198 disposed around the needle hub 196. In some embodiments, when the push button 188 is within the side hole 184, the push button 188 may hold the needle hub 196 against the bias of the spring 198.

In some embodiments, in response to depression of the push button 188, the spring 198 may be configured to expand. In some embodiments, in response to the spring 198 expanding, the telescopic barrel 178 may expand and the introducer needle 190 may be retracted into the telescopic barrel 178. In some embodiments, when the introducer needle 190 is retracted within the telescopic barrel 178, the main barrel 180 may surround the sharp distal tip 132 and/or a notch of the introducer needle 130 to reduce a risk of blood escaping the catheter system 164. In some embodiments, the push button 188 may include a distal stop surface 200 configured to contact a rim 202 of the main barrel 180 to prevent collapsing of the telescopic barrel 178 after the telescopic barrel 178 expands and the introducer needle 190 is retracted into the telescopic barrel 178. In some embodiments, the distal stop surface 200 may be perpendicular to a longitudinal axis 204 of the telescopic barrel 178. In some embodiments, the catheter system 164 may include a vent plug 206 at a proximal end of the telescopic barrel 178.

In some embodiments, the catheter system 164 may include a vent plug 206, which may allow passage of air therethrough. In some embodiments, the vent plug 206 may be disposed at a proximal end of the needle hub 196 and may allow collapsing the telescopic barrel 178 or nesting of the at least one inner sleeve 182 within the main barrel 180.

Referring now to FIGS. 13A-13F, in some embodiments, a catheter system 210 may include a catheter assembly 212, which may include a catheter adapter 214. In some embodiments, the catheter system 210 may be similar or identical to one or more of the prior art catheter system 10 of FIGS. 1-5, the catheter system 50 of FIGS. 6-8, the catheter system 108 of FIGS. 9-11, and the catheter system 164 of FIG. 12 in terms of one or more features and/or operation. In some embodiments, the catheter adapter 214 may include a distal end 216, a proximal end 218, and a catheter adapter lumen 220 extending through the distal end 216 of the catheter adapter 214 and the proximal end 218 of the catheter adapter 214. In some embodiments, the catheter assembly 212 may include a catheter 222 extending from the distal end 216 of the catheter adapter 214.

In some embodiments, the catheter assembly 212 may include a needle assembly 224. In some embodiments, the needle assembly 224 may include a barrel 226, which may include a proximal end 228, a distal end 230, and a side hole 232 between the proximal end 228 of the barrel 226 and the distal end 230 of the barrel 226.

In some embodiments, the needle assembly 224 may include an introducer needle 234, which may include a sharp distal tip 236 and a proximal end 238. In some embodiments, the introducer needle 234 may extend beyond the distal end 230 of the barrel 226 and through the catheter 222. In some embodiments, the needle assembly 224 may include a needle hub 240 affixed to the introducer needle 234. In some embodiments, the needle hub 240 may include a flexible extension 242 disposed within the side hole 232 and holding the needle hub 240 against the bias of a spring 244 disposed around the needle hub 240.

In some embodiments, the needle assembly 224 may include a lever arm 246 coupled to the barrel 226 and aligned with the side hole 232 in the barrel 226. In some embodiments, in response to depression of the lever arm 246 into the side hole 232, the lever arm 246 may release the flexible extension 242 from the side hole 232 and the spring 244 may expand. In some embodiments, in response to the expanding of the spring 244, the needle hub 240 may be moved proximally and the introducer needle 234 may be retracted.

In some embodiments, the needle hub 240 may include another flexible extension 248, which may be opposite the flexible extension 248. In some embodiments, the other flexible extension 248 may be configured to drag along an inner surface 250 of the barrel 226 in response to the expanding of the spring 244. In some embodiments, a proximal end 252 of the lever arm 246 may include a protrusion 254. In some embodiments, the flexible extension 242 may be configured to drag along the inner surface 250 of the barrel 226 in response to the expanding of the spring 244.

All examples and conditional language recited herein are intended for pedagogical objects to aid the reader in understanding the invention and the concepts contributed by the inventor to furthering the art and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed:

1. A catheter system, comprising:
a catheter assembly, comprising:
a catheter adapter, comprising a distal end, a proximal end, and a catheter adapter lumen extending through the distal end of the catheter adapter and the proximal end of the catheter adapter;
a catheter extending from the distal end of the catheter adapter;
a needle assembly, comprising:
a barrel, comprising a proximal end and a distal end;
an introducer needle, comprising a sharp distal tip and a proximal end;
a needle hub affixed to the introducer needle and movably disposed in the barrel;
a spring disposed around the needle hub;
a push button configured for selective engagement with the needle hub, wherein the push button holds the needle hub against the bias of the spring, wherein the introducer needle extends beyond the distal end of the barrel and through the catheter when the catheter adapter is adjacent to the distal end of the barrel;
a projection extending from the push button for engagement with the catheter adapter to prevent movement of the push button when the catheter adapter is adjacent to the distal end of the barrel;
an arm in connection with and extending distally from an end of the spring and contacting an inner surface of the barrel, wherein the distally-extending arm is configured to drag along the inner surface of the barrel in response to depression of the push button and expansion of the spring.

2. The catheter system of claim 1, wherein a distal end of the distally-extending arm comprises a hook.

3. The catheter system of claim 1, wherein the distally-extending arm is monolithically formed as a single unit with the spring.

4. The catheter system of claim 1, wherein the needle assembly further comprises a clip separate from the spring, wherein the clip comprises the distally-extending arm.

5. The catheter system of claim 1, wherein the distally-extending arm is a first distally-extending arm, wherein the needle assembly further comprises a second distally-extending arm opposite the first distally-extending arm.

6. The catheter system of claim 5, wherein the needle assembly further comprises a clip separate from the spring, wherein the clip comprises a coil, wherein a first end of the coil comprises the first distally-extending arm, wherein a second end of the coil comprises the second distally-extending arm.

7. The catheter system of claim 5, wherein a distal end of the first distally-extending arm comprises a hook, wherein a distal end of the second distally-extending arm comprises a another hook.

8. A catheter system, comprising:
a catheter assembly, comprising:
a catheter adapter, comprising a distal end, a proximal end, and a catheter adapter lumen extending through the distal end of the catheter adapter and the proximal end of the catheter adapter;
a catheter extending from the distal end of the catheter adapter;
a needle assembly, comprising:
a telescopic barrel, comprising a main barrel and an inner sleeve nested within the main barrel, wherein the main barrel comprises a side hole, wherein the inner sleeve comprises a distally-extending arm forming a push button within the side hole, wherein the push button is configured for selective engagement with the main barrel,
wherein the push button comprises a distal stop surface configured to contact a rim at a proximal end of the main barrel to prevent collapsing of the telescopic barrel after the telescopic barrel expands;
an introducer needle, comprising a sharp distal tip and a proximal end;
a needle hub affixed to the introducer needle and coupled to the telescopic barrel; and
a spring disposed around the needle hub, wherein when the push button is within the side hole, the push button holds the needle hub against the bias of the spring.

9. The catheter system of claim 8, wherein in response to depression of the push button, the spring is configured to expand, wherein in response to the spring expanding, the telescopic barrel expands and the introducer needle is retracted into the telescopic barrel.

10. The catheter system of claim 8, wherein the distal stop surface is perpendicular to a longitudinal axis of the telescopic barrel.

11. The catheter system of claim 8, further comprising a vent plug at a proximal end of the telescopic barrel.

* * * * *